United States Patent [19]

Mack

[11] 4,292,664

[45] Sep. 29, 1981

[54] DENTAL PLAQUE DISCLOSING LIGHT AND METHOD

[75] Inventor: William Mack, Commack, N.Y.

[73] Assignee: Clairol Incorporated, New York, N.Y.

[21] Appl. No.: 934,408

[22] Filed: Aug. 17, 1978

[51] Int. Cl.³ .................................................. B25K 23/18
[52] U.S. Cl. .................................... 362/120; 362/183; 362/157; 362/205; 362/206; 362/253; 362/293; 362/296; 362/310; 362/804
[58] Field of Search ............... 362/183, 804, 157, 293, 362/310, 296, 302, 301, 120, 109, 119, 196, 253, 205, 206; 128/21-23

[56] References Cited

U.S. PATENT DOCUMENTS

| | | | |
|---|---|---|---|
| 1,527,823 | 2/1925 | Albert | 128/23 |
| 2,565,895 | 8/1951 | Wadland | 260/6.45 X |
| 3,459,178 | 8/1969 | Fleming | 128/22 |
| 3,704,928 | 12/1972 | Coombs et al. | 362/120 |
| 3,711,700 | 1/1973 | Westlund et al. | 362/804 |
| 3,732,416 | 5/1973 | Audesse et al. | 128/123 X |
| 3,812,847 | 5/1974 | Moore et al. | 362/253 X |
| 4,195,329 | 3/1980 | Woog | 362/120 |

Primary Examiner—J. L. Barr
Attorney, Agent, or Firm—Gerald S. Rosen; George A. Mentis

[57] ABSTRACT

A dental plaque disclosing light for use in conjunction with a fluorescent dye plaque disclosing solution contained in a periodontal area of an individual's mouth is disclosed. A parabolic reflector supports a light source providing only light which causes the fluorescent dye to fluoresce. The light source is located in conjunction with the parabolic reflector to cause the parabolic reflector to project a solid, converging cone of light. Preferably, the light source is located forward of the focus of the parabolic reflector. A power supply is selectively connected to the light source for illuminating the light source. The power supply may be one or more batteries, and if the batteries are of the rechargeable type, a means for selectively recharging the batteries is connected to the batteries. A lens is supported adjacent the light source for projecting a solid, diverging cone of light having an axis concentric with the axis of the converging cone of light. A casing which supports the parabolic reflector also supports a reflecting surface adjacent the parabolic reflector such that, when the converging cone of light and diverging cone of light are directed toward the individual's mouth, the light reflected by the fluorescent dye is reflected by the reflecting surface and directed toward the individual's eyes. The light source may be a lamp and a filter means covering the lamp for filtering and passing therethrough only light which cuases the fluorescent dye to fluoresce.

24 Claims, 10 Drawing Figures

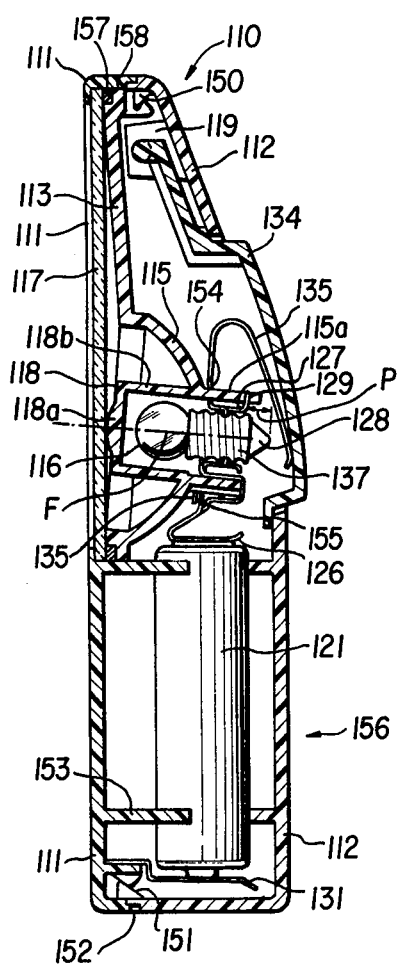
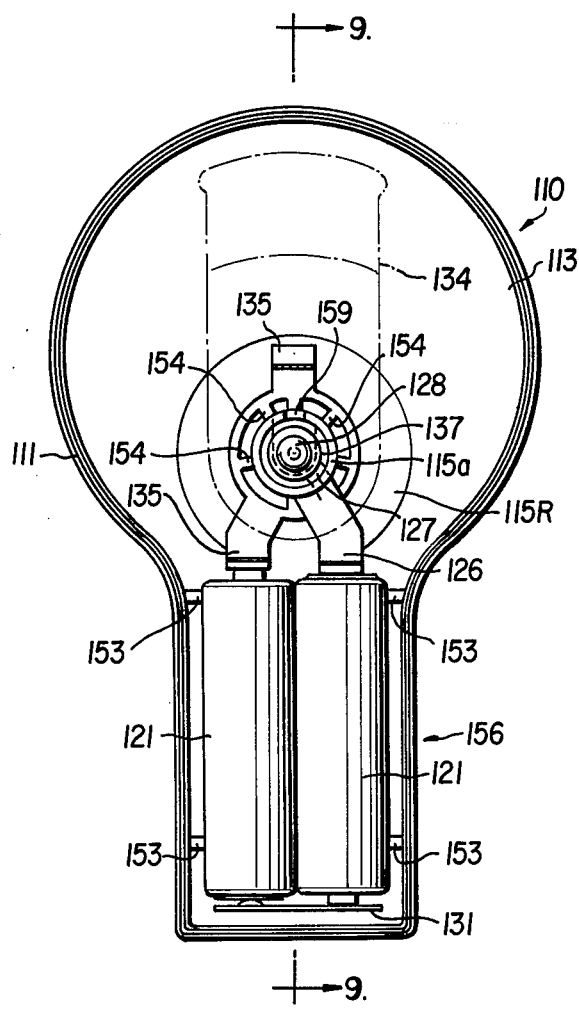
FIG. 9
FIG. 10

DENTAL PLAQUE DISCLOSING LIGHT AND METHOD

BACKGROUND OF THE INVENTION

1. Field of the Invention

This invention generally relates to an apparatus for illuminating the mouth to aid in the location and disclosure of dental plaque. More specifically, this invention relates to a pocket-size, high intensity cord or cordless appliance which, when used in conjunction with a suitable plaque-disclosing solution which is applied to the teeth, reveals instantly the presence of plaque which ordinarily may be invisible to the eye.

2. Description of the Prior Art

Heretofore, plaque diagnosis was left primarily to the dentist. This had the obvious disadvantage of allowing the patient to be informed of the presence of harmful deposits of plaque on his teeth very infrequently and only during visits to the dentist.

Recognizing the universal need for a simple plaque-disclosing method suitable for consumer use on a frequent, between-dentist-visit basis, several systems have been developed, such as U.S. Pat. Nos. 3,711,700 and 3,732,416. In addition, recently introduced are several types of plaque-disclosing devices designed for consumer use. One such device is a plaque-disclosing chemical in tablet form which, when chewed and mixed with saliva, stains the areas of the teeth where plaque is present. This system has the disadvantage of leaving an unsightly stain on the teeth for a period of time which may be considered objectionable except upon retiring.

Another device disclosed in U.S. Pat. No. 3,459,178 is in the form of a penlight flashlight with a color filter forward of its lens-end bulb. The bulb emits a narrow blue light beam to illuminate the teeth, one or two at a time, which have been previously treated with a plaque-disclosing solution. This system, with its limited scanning range, unfortunately can result in incomplete oral inspection.

Still another device, described in U.S. Pat. No. 3,704,928, utilizes a similar principle, featuring a line cord energized bulb with a dichroic reflector and color filter lens which illuminates the teeth and a dichroic mirror for viewing the teeth during illumination. This system possesses a number of deficiencies which reduce its practicality for use as a consumer appliance. It is relatively expensive and it is dependent upon an electric cord. In addition, it is too large to be carried about or stored on the narrow shelves of a bathroom medicine cabinet. Moreover, it has the functional disadvantage of emitting a beam of light of such character as to stray into the viewing mirror, which tends to partially obscure the image of the teeth in the mirror, materially reducing the effectiveness of the device.

Recent advantages in consumer oral hygienic practices, the result of availability of approved brushing and irrigation devices and the development of more effective dentifrices, through advertising, has raised the consciousness of the majority of consumers to examine and determine the effectiveness of their personal tooth maintenance habits. The word plaque, a veritable enigma to the average person only a few years ago, now, through the proliferation of TV dentifrice commercial messages, is becoming a household word. However, prior to the disclosed invention herein, there has not been a completely practical method or device available to the public which would provide a precise indication as to the extent of dental plaque involvement. Ideally, every family stands to be materially benefited by the invention described herein to the degree that they are now more able to protect themselves employing the aforementioned oral cleaning aids. While the invention described herein is so designed to lie within the means and capabilities of the mass consumer, it is recognized that the dental profession may also find the device to be an invaluable appliance which will make their diagnostic work simpler and more precise. It is contemplated that the invention disclosed herein is a breakthrough in plaque protection which may form the basis for various types of oral hygienic educational programs through a mass distribution of the unprecedented, inexpensive, easy-to-use, highly-effective means of self-examination in remedial procedures which were heretofore not regarded as being practical or feasible and which are now possible by employment of the described invention.

SUMMARY OF THE INVENTION

The invention described herein does not possess any of the foregoing disadvantages and limitations, as it departs substantially from all prior art. One embodiment of the invention features the use of one or two small, rechargeable batteries with integral charging means. The result of its small size and weight, by means of integral alternating current prongs, allows it to be plugged in and supported by any standard electrical outlet for charging and/or convenient storage between uses. This compact unit, being free of external wires and power supplies, will provide several months of daily service from an overnight charge.

Still another embodiment, which provides a lower initial cost alternative version, features the use of a pair of inexpensive, replaceable carbon zinc penlight batteries capable of providing months of service between replacements.

The use of small, inexpensive batteries is made practical through the employment of a novel, high-efficiency light projection system. A fluorescent dye plaque-disclosing solution is first applied to the teeth before use of the dental plaque disclosing light as described herein. The plaque-disclosing fluid-coated teeth are illuminated by the light via dual concentric blue light beams of a particular wavelength which excite the fluorescent dye where plaque is present, providing visual indication. The light source is a miniature, low-wattage, high-intensity, battery-powered lamp. The inner beam, an intense one-half inch diameter spot at approximately four inches, is for close examination. The outer beam of approximately two inch diameter at four inches covers all of the exposed teeth for total plaque indication and detection of the tooth areas most affected by plaque involvement, resulting from inadequate tooth cleaning procedures and techniques. The dual light beams are highly directional and, therefore, do not emit stray light which may otherwise tend to enter the user's path of vision.

Specifically, the dental plaque disclosing light described herein is for use in conjunction with a fluorescent dye plaque-disclosing solution contained in an individual's mouth. The light is comprised of a casing having a forward portion supporting a reflecting surface, a bezel connected to the forward portion and supporting a parabolic reflector, a rear housing enclosing a power supply and at least one boss removably connecting the forward portion and the rear housing.

The power supply is selectively connected to a light source for illuminating the light source. The light source emits only light which causes the fluorescent dye to fluoresce. In particular, the power supply is one or more batteries located in the casing. The batteries may be rechargeable, in which case a means for selectively recharging the batteries is connected to the batteries and located within the casing. The light source is supported in conjunction with the parabolic reflector, preferably forward of the focus on the parabolic reflector, to cause the parabolic reflector to project a solid converging cone of light having a one-half inch diameter at four inches. Lens means supported adjacent the light source projects a solid, diverging cone of light having an axis concentric with the axis of the converging cone of light and a two inch diameter at four inches. The reflecting surface is supported on the front portion of the casing adjacent the parabolic reflector so that when the converging cone of light and diverging cone of light are directed toward the individual's mouth, the light reflected by the fluorescent dye is reflected by the reflecting surface and directed toward the individual's eyes. In the preferred embodiment, the light source is a lamp and a filter covering the lamp for filtering and passing therethrough only light which causes the fluorescent dye to fluoresce. The filter is a dual-function, blue color filter lens having blue filtering sides and an end integrally connected to the sides which is a plano-convex blue filtering lens. An optically inert primary lens may be connected to and located over a portion of the parabolic reflector and the parabolic reflector may terminate in a neck portion within which the lamp is located and supported in position forward of the focus. Preferably, the reflecting surface, the parabolic reflector and the light source are an integral unit supported by the front portion of the casing in a lower portion of the casing which functions as a handle.

It is an object of this invention to provide a dental plaque disclosing light which is battery powered and may be hand held for use in conjunction with a fluorescent dye plaque disclosing solution contained in an individual's mouth.

It is a further object of this invention to provide a dental plaque disclosing light which employs dual concentric blue light beams of a particular wavelength which excite a special coating where plaque is present, providing visual indication.

It is another object of this invention to provide a rechargeable dental plaque disclosing light which employs a parabolic reflector in combination with a plano-convex lens to provide dual concentric blue light beams.

It is a further object of this invention to provide a dental plaque disclosing light having a reflective surface supported on a casing so that when light is directed toward an individual's mouth, the light reflected by a fluorescent dye plaque-disclosing solution in the mouth is reflected by the reflective surface and directed toward the individual's eyes.

It is another object of this invention to provide a dental plaque disclosing light which employs a light source comprised of a lamp and a dual function blue color filter lens covering the lamp, the filter lens having blue filtering sides and an end integrally connected to the sides which is a plano-convex blue filtering lens.

It is still another object of this invention to provide a dental plaque disclosing light employing a parabolic reflector and a light source located forward of the focus of the parabolic reflector.

BRIEF DESCRIPTION OF THE DRAWINGS

These objects and features of this invention as well as others will become apparent to those skilled in the art by referring to the accompanying specification and drawings wherein:

FIG. 9 is a longitudinal sectional view taken along line 9—9 of FIG. 10 of the preferred embodiment of the invention; and FIG. 10 is a rear view of the preferred embodiment of FIG. 9 with the rear casing removed and parts broken away.

DETAILED DESCRIPTION OF THE INVENTION

Figure 1:
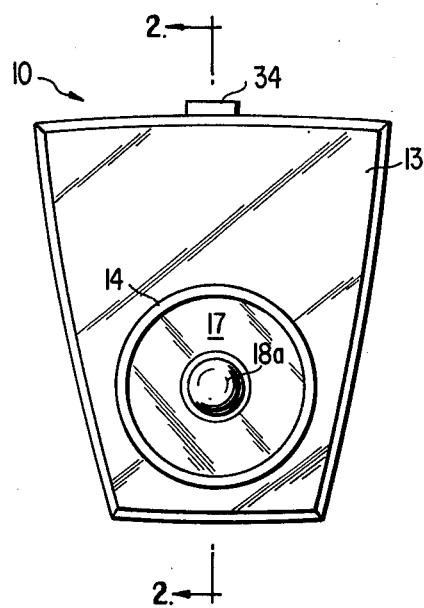
FIG. 1 is a front view of one embodiment of the dental plaque disclosing light embodying the invention.
Figure 2:
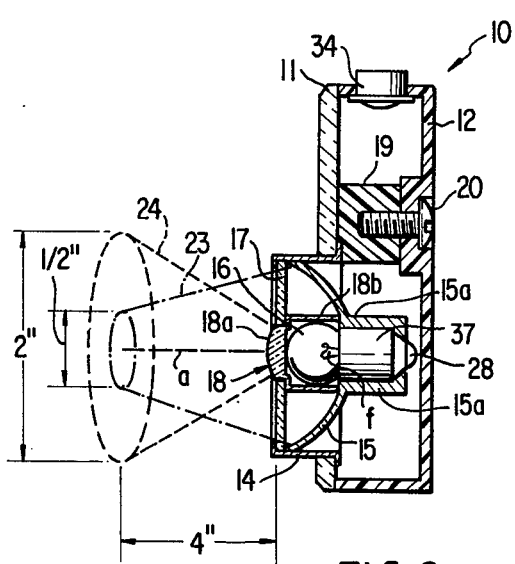
FIG. 2 is a longitudinal sectional view taken along lines 2—2 of FIG. 1 not illustrating the electrical components.

Referring to the drawings, reference character 10 generally designates an assembly comprising one embodiment of the dental plaque disclosing light of the invention. The casing of the dental plaque disclosing light is comprised in part of a separable forward portion 11 together with a rear housing 12. The forward portion 11 of the invention is a removable assembly having a partial mirrored front illustrated as reflecting surface 13. The mirrored front may be one of "keystone" shape which corresponds to the contour of the rear housing 12. The lower part of the front portion 11 has a circular opening therein into which is fitted a bezel 14 for supporting a silvered parabolic reflector 15. The parabolic reflector 15 terminates in a neck portion which functions as a lamp holder 15a. A light source, such as a miniature bulb 16, is disposed within the lamp holder 15a.

As an alternative, an optically inert primary lens 17, such as a clear glass lens, may be located over a portion of the parabolic reflector 15. As a filtering means is required to control the wavelength of the light emitted from the light source, a dual function blue color filter lens 18 may be employed. The lens 18 has blue filtering sides 18b and an end integrally connected to the sides which is a plano-convex blue filtering lens 18a. One purpose of the optically inert primary lens 17 is to cover the parabolic reflector 15 and protect the reflective silvered surface of the parabolic reflector 15. The optically inert primary lens 17 may also have an aperture therein through which the plano-convex blue filtering lens 18a projects and is supported.

On the central axis of the rear side of forward portion 11 is an integral rearward depending, internally-threaded boss 19 which is captured by a screw 20 passing through a corresponding counterbored hole in the rear housing 12, thereby forming a solid assembly between forward portion 11 and rear housing 12. Removal of the screw 20 best provides access to the batteries 21 of FIG. 4 or the rechargeable batteries 22 of FIG. 5. Access to the bulb 16 is also provided for service and/or replacement. Small alignment bosses of conventional design (not shown) may be provided to further promote the assembling of the front portion 11 to rear housing 12.

Lamp 16 has an emitting filament which is positioned slightly forward of the focus f of the parabolic reflector 15 as to project a small, solid, intense converging cone of light 23 of one-half inch diameter at about four inches from the parabolic reflector. Surrounding lamp 16 is a cylindrical portion of blue filtering sides 18b which is an integral part of the transparent dual function blue color filter lens 18 which filters light emitted from the lamp filament at a predetermined wavelength, which is compatible with the plaque-disclosing solution to be employed. The light passing through the blue filtering sides 18b strikes the parabolic reflector and therefrom passes through the optically inert primary lens 17.

The end of the dual function blue filter lens 18 is a plano-convex lens 18a which filters the filament emissions of lamp 16 as it projects a solid cone of diverging blue light 24 of two inches in diameter at about four inches from the parabolic reflector. The diverging cone of light 24 has an axis a which is concentric with the axis a of the converging cone of light 23. A neck portion which is an integral molded rearward projecting cylindrical portion 15a of the parabolic reflector 15 frictionally grips the lamp shell 37. The portion 15a is provided with a side opening 25 which permits electrical contacts 26 in FIG. 4 and 27 in FIG. 5 to make contact with the lamp shell 37. Center lamp contact 28 of the lamp 16 makes electrical connection with the spring preloaded electrical contact members 29 in FIG. 4 and 30 in FIG. 5.

Figure 4:
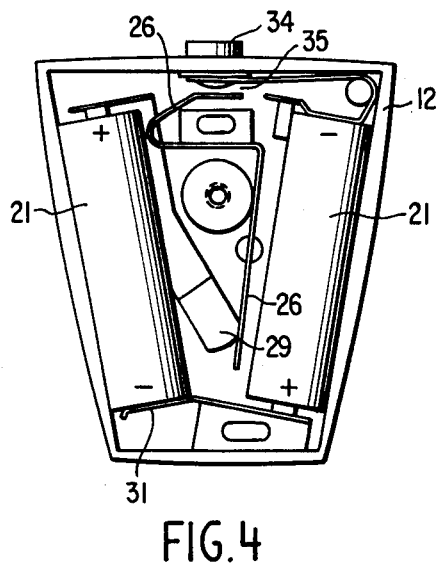
FIG. 4 is a front view, forward position removed, of a non-rechargeable embodiment of the dental plaque disclosing light, with electrical components contained therein exposed.

Referring to the embodiment illustrated in FIG. 4, the rear housing 12 encloses a pair of disposable primary batteries 21. The batteries may be any conventional penlight batteries, such as carbon zinc batteries, and may be interconnected by interconnecting conductor strip 31. Side lamp contact 26 and rear lamp contact 29 connect the batteries 21 to the lamp 16. In order to selectively illuminate the lamp 16, contact 35 and switch button 34 are utilized.

Figure 5:
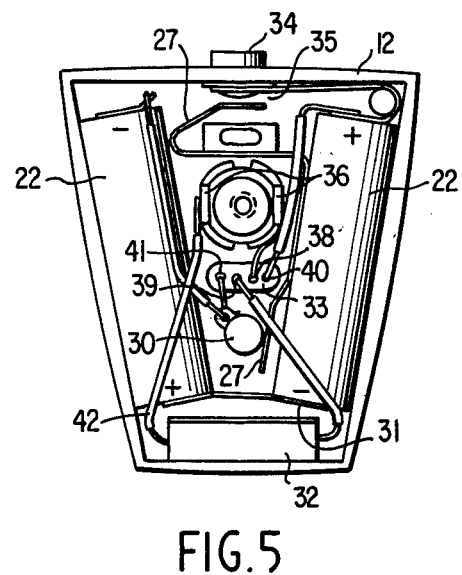
FIG. 5 is a front view, forward position removed, of a rechargeable embodiment of the dental plaque disclosing device, with electrical components contained therein exposed.
Figure 6:
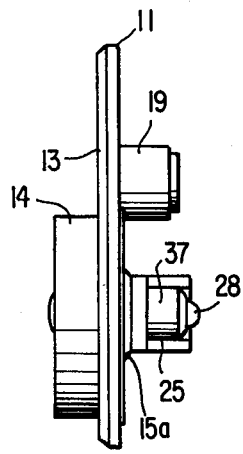
FIG. 6 is a side elevation of FIG. 1 showing the front portion of the casing separated from the rear housing of the casing.
Figure 7:
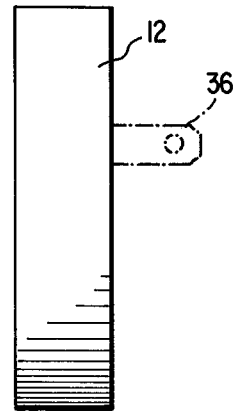
FIG. 7 is a side elevation of FIG. 1 showing the rear housing of the casing separated from the front portion of the casing.
Figure 8:
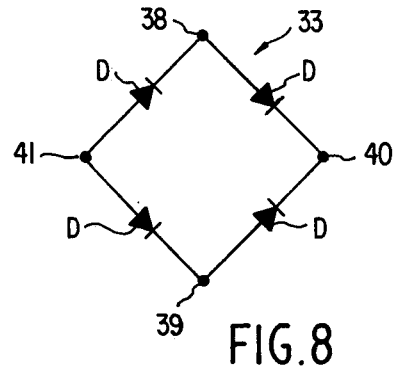
FIG. 8 is a schematic diagram of the full wave rectifier bridge employed in the rechargeable embodiment illustrated in FIG. 5.

As illustrated in FIG. 5, the rechargeable embodiment of the dental plaque disclosing light is comprised of a pair of interconnected rechargeable batteries 22 which may be any conventional rechargeable batteries such as nickel cadmium batteries. A recharging means for the batteries 22 is employed, the recharging means comprised of a voltage dropping capacitor 32 and a full wave bridge rectifier 33. The recharging means terminates in a pair of alternating current prongs 36 depending rearwardly from the rear housing 12 of the casing. Switch button 34 and contacts 35 are provided to selectively illuminate the lamp 16 via lamp contacts 27 and 30. As can be seen by comparing FIGS. 4 and 5, the embodiments respectively disclosed therein are identical except for the battery types and other related electrical components and connections. The full wave bridge rectifier 33, an embodiment of which is illustrated in FIG. 8, may be a conventional diode bridge comprised of four diodes D. In general, contact point 41 is connected to center lamp contact 30, contact point 40 is connected to the rechargeable battery 22, contact point 39 is connected to the voltage dropping capacitor 32 and contact point 38 is connected to one of the alternating current prongs 36. The other of the AC prongs is connected to voltage dropping capacitor 32 via a conductor 42. The reactance, recharging means and the types and quantities of batteries illustrated herein are disclosed as part of the preferred embodiment construction. However, other battery types and their arrangements, and alternate charging circuits may be employed without departing from the spirit and scope of the invention described herein. Electrical contacts 26, 27, 29 and 30 are supported, positioned and retained in the rear housing 12 by means of integral molded bosses.

DESCRIPTION OF THE PREFERRED EMBODIMENT

Referring to FIGS. 9 and 10, the dental plaque disclosing light is generally referred to by reference character 110. The casing of the light includes forward portion 111 and rear portion 112, which are engaged by pivot catch 150 and snap catch 151. A coin slot 152 is provided so that the rear housing 112 can be separated from the forward portion 111 and the snap catch 151 can be disconnected. This allows the rear housing 112 to be pivoted about the pivot catch 150 to provide access to the internal portions of the disclosing light 110.

The lower part of the light 110 includes a handle 156 which encases batteries 121. The forward portion of the casing includes contoured bosses 153 which cradle the batteries 121 and hold them in position. An interconnecting conductive strip 131 is supported by a boss to complete the series connection between the batteries 121. Bosses 119 are provided on the rear housing 112 to hingedly support the push button 134.

One special feature of the embodiment of the light 110 shown in FIGS. 9 and 10 is the integral formation of a reflecting surface 113, a silvered parabolic reflector 115 and a dual-function blue color light filter lens 118. This integral single unit is mounted along with a crystal 117 in the forward portion 111 of the casing. The crystal 117 and the integral unit are separated by a resilient seal 157 and the reflecting surface 113 is ultrasonically welded at 158 to the forward portion 111 of the casing. The rear of the silvered parabolic reflector 115R extends away from the parabolic reflector 115 to form a lamp holder 115a. A bulb 116, which functions as a light source, is threaded into a split ring 127 and the split ring and bulb are inserted into the lamp holder 115a.

Spring battery contact clip 126 is snapped onto the lamp holder 115a and held in place by barbs 155. The split ring 127 is configured so that it will always grasp the lamp shell 137 at the same point. Therefore, as the lamp bulb 116 and split ring 127 are inserted into the lamp holder 115a, the split ring 127 contacts the upper portion of the spring clip 126 which results in the positioning of the filament of the bulb 116 slightly forward of the focus F. This also results in the lamp contact 128 being within a predetermined axial position P, allowing contact with a spring clip 135. The spring clip 135 is also snapped onto the lamp holder 115a and held in place by barb 154. By depressing the push button 134, the spring clip is forced to contact the lamp contact 128, thereby closing the connection between the lamp and the batteries and illuminating the lamp. Preferably, the barbs 154 and 155 are angled to be self-locking and prevent removal of the spring clip 126 and the spring contact 135. The split ring 127 may be provided with a stop tab 129 which specifically slides within a notch 159 located in the upper portion of lamp holder 115a to facilitate removal of the lamp and split ring assembly and to aid in the positioning of the filament forward of the focus F.

The dual-function blue light color filter lens 118 has blue filtering sides 118b and a plano-convex blue filtering lens 118a which filter the light emitted from the bulb 116 so that only the light of the wavelength required to fluoresce the dye being used is reflected by the silvered parabolic reflector 115.

It is also contemplated that reflecting surface 113 may be separate from the silvered parabolic reflector 115 or hinged to the parabolic reflector 115 so that one can be swiveled with respect to the other (or from side to side) to vary the angle between the light beams emitted and the reflecting surface 113. It is also contemplated that the reflecting surface 113 may be flat or convex as well as concave, as shown in FIG. 9. Therefore, the reflective angle between the reflecting surface 113 and the beams of light can be adjusted depending on the type of structure which is employed in the embodiment. It is further contemplated that the casing may be configured to be waterproof to prevent leakage of water into the disclosing light 110.

Figure 3:
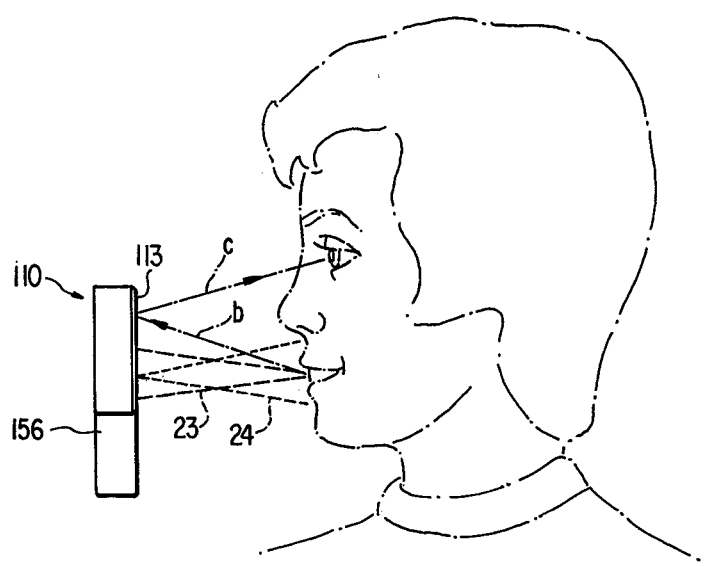
FIG. 3 is a side elevation of the dental plaque disclosing device of FIG. 9 shown in operating position relative to an individual user.

Referring to FIG. 3, the relative position between the mirrored front 13 and 113 and the reflecting and projecting surfaces of the dental plaque disclosing light 10 and 110, respectively, is such that, when the appliance is held at four inches perpendicular to the individual user's mouth, a reflected image of blue light in the illuminated mouth is in perfect alignment with the individual user's eyes. In particular, the blue light illuminated mouth image is reflected along line b to the mirrored front 113 which is then reflected to the eye of the individual user along line c.

With close range light projection as employed in the dental plaque disclosing light, the parabolic reflector 15 or 115 alone does not provide sufficient satisfactory results. This is because if the focal length of the parabolic reflector 15 or 115 were to lie on the individual user's mouth, the beam of light produced would be an intense solid cone of insufficient diameter to be useful in locating all the plaque affected areas of the teeth. As a comparison, the result of using only the parabolic reflector 15 or 115 would be similar to an attempt to locate a small object dropped on the floor in a dark room with only a penlight flashlight. If the focal length of the reflector were to be increased, the beam of light reaching the individual user's mouth would then appear as a ragged, hollow cone of light comprised of a multiplicity of enlarged, projected images of the lamp filament, appearing end to end in a circle, which tends to produce undesirable caustic cusps and filament striations about a dark central cone.

Through the use of a simple condensing lens, such as plano-convex lens 18a or 118a positioned forward of the lamp 16 or 116, respectively, a solid cone of light is projected. However, this cone of uniform density light only serves to illuminate the total oral area with a relatively low, inadequate level of light due to the limited available illumination from a small battery supply necessitated by the physical size of the dental plaque disclosing light.

This invention, on the other hand, describes a lamp 16 or 116 positioned slightly forward of a parabolic reflector focus point f or F, respectively, so as to effect a projection of a small, intense solid cone of light 23 at the central portion of the oral area being explored for close inspection of a few teeth at a time. A small condensing lens positioned directly forward of the lamp 16 or 116 so as to project a wider, solid cone of light 24 of somewhat low intensity, which, being concentric with the primary beam of intense light 23, covers the entire oral area. The latter spread beam 24 serves as a means for rapidly locating problem areas, while the narrow, intense beam 23 pinpoints the precise location and extent of plaque buildup as to aid in its removal.

Therefore, the dental plaque disclosing light described herein embodies several dimensional and locational features which are critical. Specifically, as noted above, the location of the filament of the lamp 16 or 116 forward of the focus f or F, respectively, is a critical feature of the preferred embodiment. In addition, the dimensional characteristics of the cones of light 23 and 24 is similarly a critical feature of the preferred embodiment of the invention. By providing a converging cone of light 23 which has a diameter of one-half inch at four inches from the parabolic reflector 15, an intense cone of light can be provided for close inspection of a few teeth at a time. Contemplated increases in the half-inch diameter of the cone 23 at four inches necessarily reduces the intensity below an effective level. Contemplated decreases in the half-inch diameter necessarily results in a beam of light which illuminates an insufficient area for inspection. A similar result is true with regard to the two inch diameter of the diverging cone of light 24 at four inches from the parabolic reflector 15 or 115. Increasing the two inch diameter results in light rays affecting the individual user's eyes and decreasing the two inch diameter provides insufficient illumination of the entire mouth and prevents rapid location of problem areas.

Regarding the type of dye plaque disclosing solution employed with the dental plaque disclosing light, any conventional pastes or powders that are topically applied, or chewable foodstuffs, which contain a normally invisible constituent that fluoresces and becomes easily visible when activated by a proper light source may be employed. There are many such constituents available, such as described in U.S. Pat. No. 3,309,274, incorporated herein by reference, which notes the use of fluorescent dyes in dental diagnostic methods. Almost all of the constituents are either natural or synthetic food or drug and cosmetic colors which have been certified as safe for use on or consumption by humans by the U.S. Government Food and Drug Administration. Other such materials are chemical substances known as "optical brighteners" which are normally colorless in a non-activated state, but which make such pathological disorders as dental cavities, plaque, gingival aberrations, etc., stand out by comparison with the adjoining teeth which are caused thereby to appear much whiter then ever before.

None of these colors or brighteners, when applied to diseased areas of the body, is readily visible to the unaided eye unless properly excited so as to cause them to fluoresce. Such excitation preferably is provided by a dental plaque disclosing device as described herein, which is specific for the particular fluorescent material employed. When properly excited, these colors or brighteners glow and are very easily discernible. Since those materials have an affinity for any soft, pulp-like tissues, such as plaque, and for sticking in crevices, such as develop around the dental fillings and appliances, those areas will be caused to glow. Healthy tissues in the oral cavity and in many of the regions of the body appear to resist deposition of these fluorescent materials, and are therefore not subjected to the same glowing appearance. Distinguishing the areas containing disease causing foreign matter, such as plaque, from the healthy regions thus becomes simple.

MODE OF OPERATION OF THE INVENTION

A fluorescent dye plaque-disclosing solution is applied to the teeth of an individual user by means of a fluorescent mouthwash, chewable food, solution, paste or similar vehicle. Depending on the fluorescent dye, the dual-function blue color filter lens 18 is selected to filter and pass therethrough only light which causes the fluorescent dye to fluoresce. The dye tends to adhere to the plaque covered portions of the teeth of the individual user. The individual user holds the dental plaque disclosing light 10 or 110 approximately four inches from his or her face, and depresses the switch button 34 or 134, respectively, which completes the circuit by connection with spring contact 35 or 135 connecting the power source to the light source, causing a solid cone of diverging light 24 and an intense cone of converging light 23 to be directed toward the user's mouth. The result is that the image of the plaque covered areas is reflected along line b and by mirrored surface 13 or 113 along line c to the user's eyes for location and further treatment.

In effect, by employing the dental plaque disclosing light 10 or 110 described herein, an individual is employing a method of locating plaque in his or her mouth which comprises the steps of:

applying a fluorescent dye plaque disclosing solution to the individual's mouth.

illuminating a portion of the individual's mouth with an intense beam of light of a wavelength which causes the dye to fluoresce; and simultaneously illuminating the individual's entire mouth with a second beam of light of a wavelength which causes the dye to fluoresce, thereby allowing another individual or the individual himself or herself by use of a reflecting surface to locate those portions of the individual's mouth to which the dye has adhered and, therefore, where plaque is located.

Various changes may be made in the details of the invention, as disclosed, without sacrificing the advantages thereof or departing from the scope of the appending claims. For example, it is contemplated that the intense converging cone of light 23 may be formed by means of a lens system and that the solid cone of diverging light 24 may be formed by means of a reflecting device. It is also contemplated that the light source may be located remotely from the means forming the beams of light by such techniques as fiber optics or plural mirrors. Additionally, the dye plaque disclosing solution may be any suitable solution which presents unique characteristics under specific light wavelengths and which will adhere most readily to plaque. In such a case, the wavelength of the light employed in the dental plaque disclosing light would be a wavelength which causes the dye plaque disclosing solution to exhibit these unique properties. Alternatively, a filtering means may not be necessary if the light source emits only light which causes the dye to exhibit the unique properties. Furthermore, although the present invention has been disclosed and discussed with particular regard to its exceptional advantages in terms of dental plaque disclosing, it may be understood that the invention may be employed in several applications wherein a means or method for making readily visible foreign matter, such as microcosms, tartar, materia alba, and the like, is required.

What is claimed is:

1. A dental plaque disclosing light for use in conjunction with a fluorescent dye plaque disclosing solution contained in an individual's mouth, said dental plaque disclosing light comprising:
   a. a casing;
   b. a light source emitting only light which causes the fluorescent dye to fluoresce;
   c. a power supply selectively connected to the light source for illuminating the light source;
   d. a parabolic reflector supported by the casing having a focus, the light source supported in conjunction with the parabolic reflector to cause the parabolic reflector to project a solid converging cone of light; and
   e. lens means supported adjacent the light source for projecting a solid, diverging cone of light having an axis concentric with the axis of the converging cone of light.

2. The dental plaque disclosing light of claim 1 wherein a reflecting surface is supported on the casing adjacent the parabolic reflector whereby when the converging cone of light and diverging cone of light are directed toward the individual's mouth, the light reflected by the fluorescent dye being reflected by the reflecting surface is directed toward the individual's eyes.

3. The dental plaque disclosing light of claim 2 wherein the light source is a lamp and a filter means covering the lamp for filtering and passing therethrough only light which causes the fluorescent dye to fluoresce.

4. The dental plaque disclosing light of claim 3 wherein the filter means is a dual-function blue color filter lens having blue filtering sides and an end integrally connected to the sides which is a plano-convex blue filtering lens.

5. The dental plaque disclosing device of claim 4 wherein the light source is located forward of the focus of the parabolic reflector.

6. The dental plaque disclosing light of claim 5 wherein the power supply is one or more batteries located in the casing.

7. The dental plaque disclosing light of claim 6 wherein one or more of the batteries is rechargeable and a means for selectively recharging the battery is connected to the battery and located in the casing.

8. The dental plaque disclosing light of claim 6 wherein, at an axial distance of substantially four inches from the parabolic reflector, the diameter of the converging cone of light is substantially one-half inch and the diameter of the diverging cone of light is substantially two inches.

9. The dental plaque disclosing light of claim 8 wherein an optically inert primary lens is connected to and located over a portion of the parabolic reflector and the parabolic reflector terminates in a neck portion within which the lamp is located and supported in position forward of the focus.

10. The dental plaque disclosing light of claim 9 wherein the casing is comprised of a forward portion supporting the reflecting surface, a bezel connected to the forward portion and supporting the parabolic reflector, a rear housing enclosing the power supply, and at least one boss removably connecting the forward portion and the rear housing.

11. The dental plaque disclosing light of claim 9 wherein the reflecting surface, the parabolic reflector, the neck portion and the dual-function blue color filter lens are integral with each other.

12. The dental plaque disclosing light of claim 11 wherein a spring clip is located on the neck portion and a push button is supported by the casing whereby depression of the push button causes the spring clip to contact the lamp completing a circuit to the batteries and illuminating the lamp.

13. The dental plaque disclosing light of claim 12 wherein a lower portion of the casing forms a handle within which the batteries are supported.

14. The dental plaque disclosing light of claim 13 wherein the optically inert primary lens is connected to the parabolic reflector and the reflecting surface by a resilient seal and the reflecting surface is ultrasonically welded to the casing.

15. The dental plaque disclosing light of claim 14 wherein the casing is comprised of a forward portion and a rear housing which are connected by a pivot catch and a snap catch.

16. The dental plaque disclosing light of claim 1 wherein the light source is a lamp and a filter means covering the lamp for filtering and passing therethrough only light which causes the fluorescent dye to fluoresce.

17. The dental plaque disclosing light of claim 16 wherein the filter means is a dual-function blue color filter lens having blue filtering sides and an end integrally connected to the sides which is a plano-convex blue filtering lens.

18. The dental plaque disclosing device of claim 1 wherein the light source is located forward of the focus of the parabolic reflector.

19. The dental plaque disclosing light of claim 1 wherein the power supply is one or more batteries located in the casing.

20. The dental plaque disclosing light of claim 19 wherein one or more of the batteries is rechargeable and a means for selectively recharging the battery is connected to the battery and located in the casing.

21. The dental plaque disclosing light of claim 1 wherein an optically inert primary lens is connected to and located over a portion of the parabolic reflector and the parabolic reflector terminates in a neck portion within which the light source is located and supported in position forward of the focus.

22. The dental plaque disclosing light of claim 1 wherein, at an axial distance of substantially four inches from the parabolic reflector, the diameter of the converging cone of light is substantially one-half inch and the diameter of the diverging cone of light is substantially two inches.

23. A dental plaque disclosing light for use in conjunction with a dye plaque disclosing solution contained in an individual's mouth, said dental plaque disclosing light comprising:
 a. a casing;
 b. a light source emitting only light which causes the dye to excite and provide visual indication;
 c. a power supply selectively connected to the light source for illuminating the light source;
 d. a first means supported by the casing and in conjunction with the light source for projecting a first solid beam of light having a diameter of approximately two inches at an axial distance of substantially four inches from the source; and
 e. a second means supported adjacent the light source for projecting a second solid beam of light having an axis concentric with the axis of the first solid beam, the second solid beam having a diameter of approximately one-half inch at an axial distance of approximately four inches from the source.

24. The dental plaque disclosing light of claim 23 wheren the second means is a parabolic reflector and the first means is a plano-convex lens.

* * * * *